(12) United States Patent
Lorbert et al.

(10) Patent No.: US 8,476,427 B2
(45) Date of Patent: Jul. 2, 2013

(54) PREPARATION OF METHIONINE OR SELENOMETHIONINE FROM HOMOSERINE VIA A CARBAMATE INTERMEDIATE

(75) Inventors: Stephen J. Lorbert, St. Charles, MO (US); Kevin A. Trankler, St. Charles, MO (US); Richard Vonder Embse, St. Charles, MO (US); Dayna L. Turner, St. Charles, MO (US); Tracy Rode, St. Charles, MO (US); James C. Peterson, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 188 days.

(21) Appl. No.: 13/043,740

(22) Filed: Mar. 9, 2011

(65) Prior Publication Data

US 2011/0224430 A1   Sep. 15, 2011

Related U.S. Application Data

(60) Provisional application No. 61/312,020, filed on Mar. 9, 2010, provisional application No. 61/312,012, filed on Mar. 9, 2010, provisional application No. 61/333,915, filed on May 12, 2010, provisional application No. 61/312,024, filed on Mar. 9, 2010.

(51) Int. Cl.
*C07D 265/10* (2006.01)
*C07C 391/00* (2006.01)
*C07C 319/14* (2006.01)

(52) U.S. Cl.
USPC .............................. 544/97; 562/556; 562/559

(58) Field of Classification Search
USPC ..................................... 544/97; 562/556, 559
See application file for complete search history.

(56) References Cited

U.S. PATENT DOCUMENTS

| | | | |
|---|---|---|---|
| 5,344,767 | A | 9/1994 | Boullais et al. |
| 6,194,616 | B1 | 2/2001 | Spagnol et al. |
| 6,215,024 | B1 | 4/2001 | Choudary et al. |
| 7,368,600 | B2 | 5/2008 | Hateley et al. |
| 7,381,416 | B2 | 6/2008 | Erdelmeir et al. |
| 7,884,240 | B2 | 2/2011 | Hateley et al. |
| 7,906,513 | B2 * | 3/2011 | Moore et al. ............ 514/249 |

OTHER PUBLICATIONS

Bhanage et al., "Non-Catalytic clean synthesis route using urea to cyclic urea and cyclic urethane compounds", Green Chemistry, 2004, pp. 78-80, vol. 6.
Jagtap et al. "Heterogenous base catalyzed synthesis of 2-oxazolidinones/2-imidiazolidinones via transesterification of ethylene carbonate with beta-aminoalcohols/1,2-diamines", Applied Catalysis A: General; 2008, pp. 133-138, vol. 341, Issues 1-2.
Karnbrock et al., "A New Efficient Synthesis of Acetyltelluro- and Acetylselenomethionine and Their Use in the Biosynthesis of Heavy-Atom Protein Analogs", Journal of the American Chemical Society, 1996, pp. 913-914, vol. 118, No. 4.
Montalbetti et al., "Amide Bond Formation and peptide coupling", Tetrahedron, 2005, pp. 10827-10852, vol. 61, No. 46.
Narender et al., "Liquid phase acylation of amines with acetic acid over HY zeolite", Green Chemistry, 2000, pp. 104-105, vol. 2.
Prasad et al., "Convenient, Cost-Effective, and Mild Method for the N-Acetylation of Anilines and Secondary Amines", Synthetic Communications, 2005, pp. 1189-1185, vol. 35, No. 9.
Foglino et al., "A direct sulfhydrylation pathway is used for methionine biosynthesis in *Pseudomonas aeruginosa*", Microbiology, 1995, pp. 431-439, vol. 141.
International Search Report and Written Opinion from related International Patent Application No. PCT/US11/27641, dated May 16, 2011, 12 pages.
International Search Report and Written Opinion from related International Patent Application No. PCT/US11/27642, dated May 16, 2011, 13 pages.
Mohan et al., "Zeolite catalyzed acylation of alcohols and amines with acetic acid under microwave irradiation", Green Chemistry, 2006, pp. 368-372, vol. 8, Abstract Only.
Selva et al., "A Simple One-Pot Synthesis of Functionalized Ketimines from Ketones and Amine Hydrochloride Salts", Synthetic Communications: An International Journal for Rapid Communication of Synthetic Organic Chemistry, 1995, pp. 369-378, vol. 25, No. 3, Abstract Only.

* cited by examiner

*Primary Examiner* — Kahsay T Habte
(74) *Attorney, Agent, or Firm* — Polsinelli PC

(57) ABSTRACT

Provided herein are processes for the production of methionine or selenomethionine from homoserine. In particular, the processes proceed via the production of carbamate intermediates.

28 Claims, No Drawings

PREPARATION OF METHIONINE OR SELENOMETHIONINE FROM HOMOSERINE VIA A CARBAMATE INTERMEDIATE

CROSS-REFERENCE TO RELATED APPLICATION

This application claims priority to U.S. Provisional Application Ser. No. 61/312,024 filed on Mar. 9, 2010; U.S. Provisional Application Ser. No. 61/312,020 filed on Mar. 9, 2010; U.S. Provisional Application Ser. No. 61/312,012 filed on Mar. 9, 2010; and U.S. Provisional Application Ser. No. 61/333,915 filed on May 12, 2010, each of which is hereby incorporated by reference in their entirety.

FIELD OF THE INVENTION

The present invention relates to the synthesis of methionine or selenomethionine from homoserine, wherein the synthesis pathway proceeds via the production of a carbamate intermediate.

BACKGROUND OF THE INVENTION

Methionine is utilized in a variety of fields, from pharmaceuticals to health and fitness products to feed supplements. Selenomethionine is also commercially important because it is a natural source of selenium. Methionine is produced industrially in large amounts; it is currently produced by a completely synthetic pathway that utilizes petroleum-based chemicals and hazardous chemicals. Because of price increases in petroleum, the high costs associated with hazardous waste management, as well as for safety and environmental reasons, there exists a need for alternate methionine synthesis pathways.

SUMMARY OF THE INVENTION

One aspect of the disclosure provides a process for producing a compound comprising Formula (III) or a pharmaceutically acceptable salt thereof from a compound comprising Formula (I). The process comprises contacting the compound comprising Formula (I) with a carbonyl donor to form a compound comprising Formula (II). The process further comprises contacting the compound comprising Formula (II) with a compound comprising MeZ to form the compound comprising Formula (III) or a pharmaceutically acceptable salt thereof:

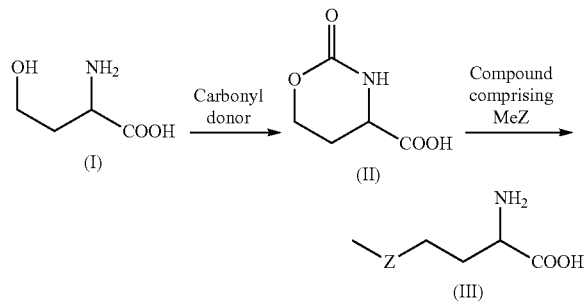

wherein:
Me is methyl; and
Z is sulfur or selenium.

Another aspect of the disclosure encompasses a process for preparing a compound comprising Formula (II) from a compound comprising Formula (I). The process comprises contacting the compound comprising Formula (I) with a carbonyl donor to form the compound comprising Formula (II):

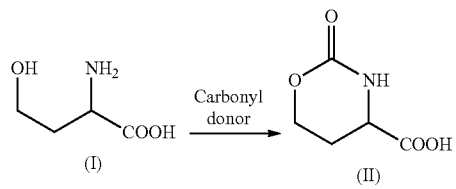

wherein:
the carbonyl donor chosen from urea, a urea derivative, a cyclic carbonate, a dialkyl carbonate, a diaryl carbonate, an alkyl carbamate, an aryl carbamate, and a halocarbonyl.

A further aspect of the disclosure provides a process for preparing compound comprising Formula (III) or a pharmaceutically acceptable salt thereof from a compound comprising Formula (II). The process comprises contacting the compound comprising Formula (II) with a compound comprising MeZ to form the compound comprising Formula (III) or a pharmaceutically acceptable salt thereof:

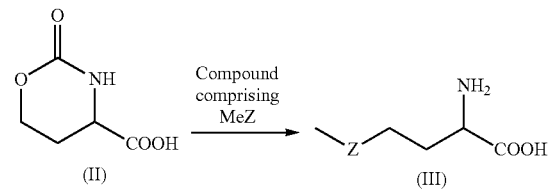

wherein:
Me is methyl; and
Z is sulfur or selenium.

Other aspects and features of the invention are described in more detail below.

DETAILED DESCRIPTION

The present invention provides processes for the preparation of methionine or selenomethionine from homoserine. In particular, methionine or selenomethionine is prepared via a pathway comprising the production of a carbamate intermediate. This synthetic process not only avoids the use of hazardous chemicals, but also utilizes homoserine, which can be prepared using fermentation processes.

(I) Preparation of a Compound Comprising Formula (III) or Salt thereof via a Carbamate Intermediate One aspect of the disclosure provides a process for preparing a compound comprising Formula (III) or pharmaceutically acceptable salt thereof from a compound comprising Formula (I), wherein the process proceeds via a carbamate intermediate. The process comprises Step A in which the compound comprising Formula (I) is contacted with a carbonyl donor to form the carbamate intermediate, i.e., a compound comprising Formula (II). The process further comprises Step B in which the compound comprising Formula (II) is contacted with a compound comprising MeZ to form the compound comprising Formula (III) or a pharmaceutically acceptable salt thereof. For the purposes of illustration, Reaction Scheme 1 depicts the preparation of the compound comprising Formula (III) or a salt thereof according to this aspect of the invention:

Reaction scheme 1:

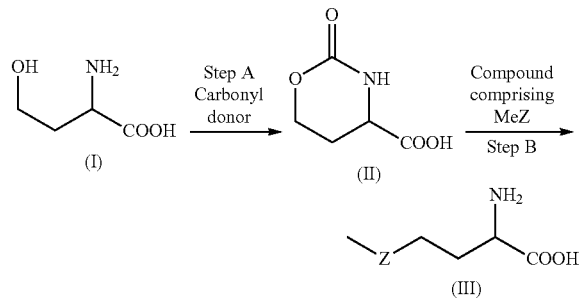

wherein:
Me is methyl; and
Z is sulfur or selenium.
(a) Step A—Reaction Mix
Step A of the process comprises contacting the compound comprising Formula (I) with a carbonyl donor to form the compound comprising Formula (II). The process commences with the formation of a reaction mixture comprising the compound comprising Formula (I) and the carbonyl donor.
(i) Carbonyl Donor
A variety of carbonyl donors may be used in Step A of the process. As used herein, a "carbonyl donor" refers to a molecule capable of donating a carbonyl group to another molecule such that a carbamate is formed. In one embodiment, the carbonyl donor may be urea or a derivative of urea. Non-limiting examples of urea derivatives include dimethyl urea, tetramethyl urea, alkyl ureas, dialkyl ureas, tetralkyl ureas, aryl ureas, and the like. In yet another embodiment, the carbonyl donor may be a cyclic carbonate. Suitable cyclic carbonates include, but are not limited to, ethylene carbonate, propylene carbonate, a butylene carbonate, a pentylene carbonate, and so forth. In yet another embodiment, the carbonyl donor may be a dialkyl carbonate such as, e.g., dimethyl carbonate, diethyl carbonate, dipropyl carbonate, and so forth. In a further embodiment, the carbonyl donor may be a diaryl carbonate (such as, e.g., diphenyl carbonate) or an alkyl aryl carbonate. In an alternate embodiment, the carbonyl donor may be an alkyl carbamate (such as, e.g., methyl carbamate) or an aryl carbamate (such as, e.g., phenyl carbamate). In yet another embodiment, the carbonyl donor may be a halocarbonyl compound. Non-limiting examples of suitable halocarbonyl compounds include phosgene, diphosgene, triphosgene, methyl chloroformate, ethyl chloroformate, propyl chloroformate, isobutyl chlorformate, and the like.

The amount of carbonyl donor that is contacted with the compound comprising Formula (I) can and will vary. In general, the molar ratio of the compound comprising Formula (I) to the carbonyl donor may range from about 1:0.1 to about 1:10. In some embodiments, the molar ratio of the compound comprising Formula (I) to the carbonyl donor may range from about 1:0.5 to about 1:5. In certain embodiments, the molar ratio of the compound comprising Formula (I) to the carbonyl donor may be about 1:0.8, 1:0.9, 1:1, 1:1.1, 1:1.2, 1:1.3, 1:1.4, 1:1.5, 1:1.6, 1:1.7, 1:1.8, 1:1.9, or 1:2.0. In one embodiment, the molar ratio of the compound comprising Formula (I) to the carbonyl donor may be about 1:1.

The reaction mixture may further comprise a base. In one embodiment, the base may be an alkylamine, a dialkylamine, or a trialkylamine. For example, the base may be methylamine, ethylamine, dimethylamine, triethylamine, and so forth. In another embodiment, the base may be ammonium hydroxide, potassium bicarbonate, potassium carbonate, potassium hydroxide, potassium t-butoxide, sodium bicarbonate, sodium carbonate, sodium hydride, sodium hydroxide, sodium methoxide, sodium ethoxide, sodium t-butoxide, or a combination thereof.

The amount of base that is added to the reaction mixture can and will vary. In general, the molar ratio of the base to the compound comprising Formula (I) may range from about 1:0.1 to about 1:10. In some embodiments, the molar ratio of the compound comprising Formula (I) to the base may range from about 1:0.5 to about 1:5. In certain embodiments, the molar ratio of the compound comprising Formula (I) to the base may be about 1:0.8, 1:0.9, 1:1, 1:1.1, 1:1.2, 1:1.3, 1:1.4, 1:1.5, 1:1.6, 1:1.7, 1:1.8, 1:1.9, or 1:2.0. In one embodiment, the molar ratio of the compound comprising Formula (I) to the base may be about 1:1.

In one preferred embodiment, the carbonyl donor is phosgene and the base is triethylamine, and molar ratio of the compound comprising Formula (I) to the carbonyl donor to the base may be about 1:1:1.

(ii) Optional Catalyst
The reaction mixture may optionally comprise a catalyst. The presence of a catalyst, as well as the type of catalyst, typically will vary as a function of the type of carbonyl donor.

For example, in embodiments in which the carbonyl donor is urea or a halocarbonyl typically no catalyst is included in the reaction mixture.

Alternatively, in embodiments in which the carbonyl donor is a cyclic carbonate, a catalyst generally is included in the reaction mixture. The catalyst may be a metal oxide. Non-limiting examples of suitable metal oxides include calcium oxide, chromium oxide, copper oxide, iron oxide, lithium oxide, magnesium oxide, manganese oxide, silver oxide, sodium oxide, titanium oxide, and zinc oxide. In one embodiment, the metal oxide may be magnesium oxide.

In embodiments in which the carbonyl donor is a halocarbonyl compound the reaction mixture may further comprise a catalyst. Suitable catalysts include proton acceptors. Non-limiting examples of suitable proton acceptors include hydroxides of alkali metals and alkaline earth metals (such as, for example, NaOH and $Ca(OH)_2$ and the like), as well as group 1 salts of carbanions, amides, and hydrides (such as, for example, butyl lithium, sodium amide ($NaNH_2$), sodium hydride (NaH), and the like).

The amount of catalyst included in the reaction mixture can and will vary. Generally, the molar ratio of the compound comprising Formula (I) to the catalyst may range from about 1:0.001 to about 1:1. In various embodiments, the molar ratio of the compound comprising Formula (I) to the catalyst may range from about 1:0.001 to about 1:0.003, from about 1:0.003 to about 1:0.01, from about 1:0.01 to about 1:0.3, from about 1:0.3 to about 1:0.1, from about 1:0.1 to about 1:0.3, or from 1:0.3 to about 1:1. In one embodiment, the molar ratio of the compound comprising Formula (I) to the catalyst may be about 1:0.15.

(iii) Solvent
Typically, the reaction mixture also comprises a solvent. The solvent may be an aprotic solvent, a protic solvent, or combinations thereof. In general, the type of solvent will vary as a function of the type of carbonyl donor used in the reaction.

Non-limiting examples of suitable aprotic solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), dioxane, N-methyl-2-pyrrolidinone (NMP), ethyl formate, ethyl methyl ketone, formamide, hexachloroacetone, hexamethylphosphoramide, ionic liquids, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. In embodiments in which the carbonyl donor is urea, the solvent may be N,N-dimethylformamide.

Examples of suitable protic solvents include, without limit, water, C1-C4 alcohols, a diol such as propylene glycol, and mixtures thereof. Examples of suitable C1-C4 alcohols include methanol, ethanol, isopropanol, n-propanol, isobutanol, n-butanol, s-butanol, t-butanol, and the like. In embodiments in which the carbonyl donor is a cyclic carbonate, the solvent may be an alcohol such as ethanol. In other embodiments in which the carbonyl donor is phosgene or a related compound, the solvent may be water.

The amount of solvent included in the reaction mixture may vary. Typically, the molar ratio of the solvent to the compound comprising Formula (I) may range from about 1:1 to about 50:1. In some embodiments, the molar ratio of the solvent to the compound comprising Formula (I) may range from about 2:1 to about 25:1. In certain embodiments, the molar ratio of the solvent to the compound comprising Formula (I) may be about 4:1, 5:1, 6:1, 7:1, 8:1, 10:1, 12:1, 14:1, 16:1, 18:1, or 20:1. In embodiments in which the carbonyl donor is urea, the molar ratio of the solvent to the compound comprising Formula (I) may be about 5:1. In embodiments in which the carbonyl donor is cyclic carbonate, the molar ratio of the solvent to the compound comprising Formula (I) may be about 10:1.

(b) Step A—Reaction Conditions

The reaction of Step A is allowed to proceed at a temperature that may range from about 20° C. to about 200° C. In certain embodiments, the temperature of the reaction may be about 25° C., 30° C., 40° C., 50° C., 60° C., 70° C., 80° C., 90° C., 100° C., 110° C., 120° C., 130° C., 140° C., 150° C., 160° C., 170° C., or 180° C. In embodiments in which the carbonyl donor is carbonyl dichloride, the temperature of the reaction may be about 30° C. In embodiments in which the carbonyl donor is urea, Step A may be conducted at a temperature of about 150° C. In embodiments in which the carbonyl donor is a cyclic carbonate, the temperature of the reaction may be about 80° C.

The pressure of the reaction can and will vary. The reaction may be conducted at a pressure ranging from about 0 psig to about 50 psig. In embodiments in which the carbonyl donor is urea, the pressure of the reaction may be about 15 psig.

In general, the reaction is allowed to proceed for a sufficient period of time until the reaction is substantially complete. For example, the duration of the reaction may range from about 5 minutes to about 10 hours. The completeness of the reaction may be determined by any method known to one skilled in the art, such as IR, HPLC, or LC-MS. In this context, a "completed reaction" generally means that the reaction mixture contains a significantly diminished amount of the compound comprising Formula (I) and a significantly increased amount of the compound comprising Formula (II) compared to the amounts of each present at the beginning of the reaction. Typically, the amount of the compound comprising Formula (I) remaining in the reaction mixture may be less than about 3%, less than about 1%, or preferably less than about 0.5%.

Upon completion of the reaction, the reaction mixture may be cooled and the compound comprising Formula (II) may be isolated by any means familiar to those of skill in the art. Suitable means include concentration, precipitation, filtration, distillation, phase extraction, preparative chromatography, crystallization, and the like. The isolated product may be washed and dried, and analyzed by means familiar to those skilled in the art.

The yield of the compound comprising Formula (II) can and will vary. Typically, the yield of the compound comprising Formula (II) may be at least about 60% w/w. In some embodiments of the invention, the yield of the compound comprising Formula (II) may be at least about 65%, 70%, 75%, 80%, or 85% w/w. In further embodiments, the yield of the compound comprising Formula (II) may be at least about 90%, 95%, 97%, or 99% w/w.

(c) Step B—Reaction Mix

The process further comprises Step B in which the compound comprising Formula (II) is contacted with a compound comprising MeZ to form the compound comprising Formula (III) or a pharmaceutically acceptable salt thereof. As used herein, the "compound comprising MeZ" refers to a compound capable of donating a methyl sulfur moiety or a methyl selenium moiety to another compound. Non-limiting examples of suitable compounds comprising MeZ include alkali metal methanethiolates, methyl mercaptan, alkali metal methaneselenoates, and methyl selenol. Typically, the alkali metal will be sodium, potassium, or lithium.

(i) Alkali Metal Methanethiolates

In some embodiments, a salt of the compound comprising Formula (III) in which Z is sulfur may be prepared by contacting the compound comprising Formula (II) with an alkali metal methanethiolate (i.e., alkali metal MeS). Suitable alkali metal methanethiolates include sodium methanethiolate, potassium methanethiolate, or lithium methanethiolate. The alkali metal methanethiolate may be purchased from a commercial chemical supply company. Alternatively, the alkali metal methanethiolate may be synthesized prior to use.

Synthesis of alkali metal methanethiolates. The alkali metal methanethiolate may be synthesized by contacting methyl mercaptan (also called methanethiol) with an alkali metal hydroxide. Suitable alkali metal hydroxides include, but are not limited to, sodium hydroxide, potassium hydroxide, and lithium hydroxide.

The amount of alkali metal hydroxide contacted with methyl mercaptan can and will vary. In general, the molar ratio of methyl mercaptan to alkali metal hydroxide may range from about 1:0.1 to about 1:10. In one embodiment, the molar ratio of methyl mercaptan to alkali metal hydroxide may be about 1:1

Typically, contact with the alkali metal hydroxide is conducted in the presence of a solvent. The solvent may be a protic solvent, an aprotic solvent, an organic solvent, or combinations thereof. Non-limiting examples of suitable protic solvents include water; an alcohol such as methanol, ethanol, isopropanol, n-propanol, isobutanol, n-butanol, s-butanol, t-butanol; a diol such as propylene glycol, and combinations thereof. Examples of suitable aprotic solvent include without limit acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), ethyl formate, ethyl methyl ketone, formamide, hexachloroacetone, hexamethylphosphoramide, ionic liquids, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. Examples of suitable organic solvents include, but are not limited to, alkane and substituted alkane solvents (including cycloalkanes), aromatic hydrocarbons, esters, ethers, ketones, and combinations thereof. Specific organic solvents that may be used include, for example, benzene, chlorobenzene, ethyl acetate, heptane, hexane, isobutylmethylketone, isopropyl acetate, toluene, and combinations thereof.

In one embodiment, the alkali metal methanethiolate may be synthesized by contacting methyl mercaptan with a solution of alkali metal hydroxide comprising DMSO. In another embodiment, methyl mercaptan may be contacted with a solution of alkali metal hydroxide comprising DMSO and toluene. In yet another embodiment, methyl mercaptan may be contacted with a solution of alkali metal hydroxide comprising an alcohol such as n-butanol.

The amount of solvent included in the reaction mix can and will vary. In general, the molar ratio of the solvent to methyl mercaptan may range from about 0.5:1 to about 10:1. In various embodiments, the molar ratio of the solvent to methyl mercaptan may be about 1:1, 2:1, 3:1, 4:1, or 5:1.

The temperature of the reaction may also vary. Typically, the temperature of the reaction will range from about 0° C. to about 40° C. In some embodiments, the temperature of the reaction may be room temperature (i.e., about 22-25° C.). Typically, the reaction will be conducted under nitrogen or argon. Upon completion of the reaction, the resultant water and/or solvent may be removed by azeotropic distillation.

Reaction with methanethiolate. Contact between the compound comprising Formula (II) and the alkali metal methanethiolate produces a salt of the compound comprising Formula (III) in which Z is sulfur. Typically, the molar ratio of the compound comprising Formula (II) to the alkali metal methanethiolate may range from about 1:0.25 to about 1:5. In some embodiments, the molar ratio of the compound comprising Formula (II) to the alkali metal methanethiolate may range from about 1:0.5 to about 1:2.5. In further embodiments, the molar ratio of the compound comprising Formula (II) to the alkali metal methanethiolate may be about 1:0.5, 1:0.6, 1:0.7, 1:0.8, 1:0.9, 1:1.0, 1:1.1. 1:1.2, 1:1.3, 1:1.4, 1:1.5, 1:1.6, 1:1.7, 1:1.8, 1:1.9, or 1:2.0. In one embodiment, the molar ratio of the compound comprising Formula (II) to the alkali metal methanethiolate may be about 1:1.1. In another embodiment, the molar ratio of the compound comprising Formula (II) to the alkali methanethiolate may be about 1:1.2.

Reaction of the compound comprising Formula (II) with the alkali metal methanethiolate is generally conducted in the presence of a solvent. The solvent may be an aprotic solvent, a protic solvent, or combinations thereof. Examples of suitable aprotic and protic solvents are listed above. In particular, the aprotic solvent may be acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, or combinations thereof. Specific protic solvents that may be used include water, a C1-C4 alcohol, a diol such as propylene glycol, and combinations thereof. In one embodiment, the solvent may be dimethyl sulfoxide. In another embodiment, the solvent may be N,N-dimethylformamide.

The molar ratio of the solvent to the compound comprising Formula (II) can and will vary. In general, the molar ratio of the solvent to the compound comprising Formula (II) may range from about 1:1 to about 50:1. In some embodiments, the molar ratio of the solvent to the compound comprising Formula (II) may be about 5:1. 10:1, 15:1, 20:1, 25:1, 30:1, 35:1, or 40:1. In one embodiment, the molar ratio of the solvent to the compound comprising Formula (II) may be about 15:1. In another embodiment, the molar ratio of the solvent to the compound comprising Formula (II) may be about 20:1. In a further embodiment, the molar ratio of the solvent to the compound comprising Formula (II) may be about 25:1.

(ii) Methyl Mercaptan

In other embodiments, the compound comprising Formula (II) may be contacted with methyl mercaptan (MeSH) to form the compound comprising Formula (III) in which Z is sulfur. The molar ratio of the compound comprising Formula (II) to methyl mercaptan may range from about 1:10 to about 1:150. In various embodiments, the molar ratio of the compound comprising Formula (II) to methyl mercaptan may be about 1:20, 1:40, 1:60, 1:80, 1:100, 1:120, or 1:140.

Reaction between the compound comprising Formula (II) and methyl mercaptan may be conducted in the presence of a catalyst. In some embodiments, the catalyst may be a proton donor having a pKa of less than 0. Non-limiting examples of proton donors having this characteristic include HCl, HBr, HI, $HClO_3$, $HClO_4$, $HBrO_4$, $HIO_3$, $HIO_4$, $HNO_3$, $H_2SO_4$, $MeSO_3H$, $CF_3SO_3H$, alkyl sulfonic acids, aryl sulfonic acids, and the like. In general, the molar ratio acid of the compound comprising Formula (II) to the catalyst may range from about 1:1 to about 1:20. In some embodiments, molar ratio of the compound comprising Formula (II) to the catalyst may be about 1:3, 1:6, or 1:9.

Contact between the compound comprising Formula (II) and methyl mercaptan may be performed in the presence of a solvent. The solvent may be a protic solvent, an aprotic solvent, an organic solvent, or mixtures thereof. Examples of suitable solvents are listed above in section (I)(c)(i). The molar ratio of the solvent to the compound comprising Formula (II) may range from about 1:1 to about 50:1. In some embodiments, the molar ratio of the solvent to the compound comprising Formula (II) may range from about 5:1 to about 25:1.

(iii) Alkali Metal Methaneselenoate

In still other embodiments, a salt of the compound comprising Formula (III) in which Z is selenium may be prepared by contacting the compound comprising Formula (II) with an alkali metal methaneselenoate (i.e., alkali metal MeSe). Suitable alkali metal methaneselenoate include sodium methaneselenoate, potassium methaneselenoate, or lithium methaneselenoate. As known to those of skill in the art, the alkali metal methaneselenoate may be prepared by a variety of methods. In one embodiment, for example, the alkali metal methaneselenoate may be prepared by contacting selenium metal with methyllithium, methylsodium, or a similar compound. In another embodiment, sodium methaneselenoate may be prepared by contacting sodium metal, sodium hydride, or sodium borohydride with dimethyldiselenide. In a further embodiment, the methaneselenoate may be prepared by contacting selenium metal with a Grignard reagent (i.e., an alkyl- or aryl magnesium halides such as methyl magnesium bromide or methyl magnesium iodide). In an alternate embodiment, the methaneselenoate may be prepared by contacting methyl selenol with a suitable base. Conditions for each of the above listed reactions are well known to those of skill in the art.

In general, the molar ratio of the compound comprising Formula (II) to the alkali metal methaneselenoate may range about 1:0.25 to about 1:5. In some embodiments, the molar ratio of the compound comprising Formula (II) to the alkali metal methaneselenoate may range from about 1:0.5 to about 1:2.5. In further embodiments, the molar ratio of the compound comprising Formula (II) to the alkali metal methaneselenoate may be about 1:0.5, 1:0.6, 1:0.7, 1:0.8, 1:0.9, 1:1.0, 1:1.1, 1:1.2, 1:1.3, 1:1.4, 1:1.5, 1:1.6, 1:1.7, 1:1.8, 1:1.9, or 1:2.0. In one embodiment, the molar ratio of the compound comprising Formula (II) to the alkali metal methaneselenoate may be about 1:1.1. In another embodiment, the molar ratio of the compound comprising Formula (II) to the alkali methaneselenoate may be about 1:1.2.

Contact between the compound comprising Formula (II) and the alkali metal methaneselenoate is generally conducted in the presence of a solvent. The solvent may be an aprotic solvent, a protic solvent, or combinations thereof. Examples of suitable aprotic and protic solvents are listed above in section (I)(c)(i). In particular, the aprotic solvent may be acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, or combinations thereof. Specific protic solvents that may be used include water, a C1-C4 alcohol, a diol such as propylene glycol, and combinations thereof. In one embodiment, the solvent may be dimethyl sulfoxide. In another embodiment, the solvent may be N,N-dimethylformamide.

The molar ratio of the solvent to the compound comprising Formula (II) can and will vary. In general, the molar ratio of the solvent to the compound comprising Formula (II) may range from about 1:1 to about 50:1. In some embodiments, the molar ratio of the solvent to the compound comprising Formula (II) may be about 5:1. 10:1, 15:1, 20:1, 25:1, 30:1, 35:1, or 40:1. In one embodiment, the molar ratio of the solvent to the compound comprising Formula (II) may be about 15:1. In another embodiment, the molar ratio of the solvent to the compound comprising Formula (II) may be about 20:1. In a further embodiment, the molar ratio of the solvent to the compound comprising Formula (II) may be about 25:1.

(iv) Methyl Selenol

In alternate embodiments, the compound comprising Formula (III) in which Z is selenium may be prepared by contacting the compound comprising Formula (II) with methyl selenol (MeSeH). The molar ratio of the compound comprising Formula (II) to methyl selenol may range from about 1:10 to about 1:150. In various embodiments, the molar ratio of the compound comprising Formula (II) to methyl selenol may be about 1:20, 1:40, 1:60, 1:80, 1:100, 1:120, or 1:140.

Reaction between the compound comprising Formula (II) and methyl selenol may be conducted in the presence of a catalyst. In some embodiments, the catalyst may be a proton donor having a pKa of less than 0. Non-limiting examples of proton donors having this characteristic include HCl, HBr, HI, $HClO_3$, $HClO_4$, $HBrO_4$, $HIO_3$, $HIO_4$, $HNO_3$, $H_2SO_4$, $MeSO_3H$, $CF_3SO_3H$, alkyl sulfonic acids, aryl sulfonic acids, and the like. In general, the molar ratio acid of the compound comprising Formula (II) to the catalyst may range from about 1:1 to about 1:20. In some embodiments, molar ratio of the compound comprising Formula (II) to the catalyst may be about 1:3, 1:6, or 1:9.

Contact between the compound comprising Formula (II) and methyl selenol may be performed in the presence of a solvent. The solvent may be a protic solvent, an aprotic solvent, an organic solvent, or mixtures thereof. Examples of suitable solvents are listed above in section (I)(c)(i). The molar ratio of the solvent to the compound comprising Formula (II) may range from about 1:1 to about 50:1. In some embodiments, the molar ratio of the solvent to the compound comprising Formula (II) may range from about 5:1 to about 25:1.

(d) Step B—Reaction Conditions

The reaction of Step B is allowed to proceed at a temperature that may range from about 20° C. to about 200° C. In certain embodiments, the temperature of the reaction may be about 30° C., 40° C., 50° C., 60° C., 70° C., 80° C., 90° C., 100° C., 110° C., or 120° C. In one embodiment, the reaction of Step B is conducted at a temperature of 50° C. In another embodiment, the reaction of Step B is conducted at a temperature of 80° C. The reaction may be conducted under ambient pressure, and under an inert atmosphere (e.g., nitrogen or argon).

In general, the reaction is allowed to proceed for a sufficient period of time until the reaction is substantially complete. Typically, the reaction may be allowed to proceed from about 5 minutes to about 10 hours. The reaction may be performed as a continuous process or a non-continuous process. The duration of the reaction may vary as a function of the temperature. For example, a reaction conducted at 50° C. may be allowed to proceed for about 5 hr; whereas a reaction conducted at 80° C. may be allowed to proceed for about 2 hr. The completeness of the reaction may be determined by any method known to one skilled in the art, such as IR, HPLC, or LC-MS. Typically, the amount of the compound comprising Formula (II) remaining in the reaction mixture may be less than about 3%, less than about 1%, or preferably less than about 0.5%.

Upon completion of Step B of the process, the reaction mixture may be cooled and the compound comprising Formula (III) or a salt thereof may be isolated by any means familiar to those of skill in the art. Suitable means include distillation, concentration, precipitation, filtration, phase extraction, crystallization, and the like. For example, the reaction mixture may be distilled to yield a distillate comprising the compound comprising Formula (III) or salt thereof. The distillate may be treated such that the compound comprising Formula (III) or its salt precipitates. The precipitated product may be isolated, washed, dried, and/or analyzed by means familiar to those skilled in the art.

The process disclosed herein may produce the compound comprising Formula (III) (i.e., a free acid) or a salt of the compound comprising Formula (III). In embodiments in which the compound comprising MeZ is an alkali metal methanethiolate of an alkali metal methaneselenoate, the compound comprising Formula (III) prepared by the process will be a salt. The salt of the compound comprising Formula (III) may be neutralized with a proton donor (e.g., HCl) to form the compound comprising Formula (III). In other embodiments in which compound comprising MeZ is methyl mercaptan or methyl selenol, the compound produced by the process will be a free acid. In such embodiments, the compound comprising Formula (III) may be converted into a salt using means well know to those of skill in the art. The compound comprising Formula (III) may have an L configuration, a D configuration, or mixture thereof.

The yield of the compound comprising Formula (III) or a pharmaceutically acceptable salt thereof can and will vary. Typically, the yield of the compound comprising Formula (III) or its salt may be at least about 60% w/w. In some embodiments, the yield of the compound comprising Formula (III) or its salt may be at least about 65%, 70%, 75%, 80%, or 85% w/w. In further embodiments, the yield of the compound comprising Formula (III) or its salt may be at least about 90%, 95%, 97%, or 99% w/w.

II. Preparation of a Compound Comprising Formula (II)

Another aspect of the disclosure encompasses a process for preparing a compound comprising Formula (II) from a compound comprising Formula (I). The process comprises contacting the compound comprising Formula (I) with a carbonyl donor to form a compound comprising Formula (II), according to the following reaction scheme:

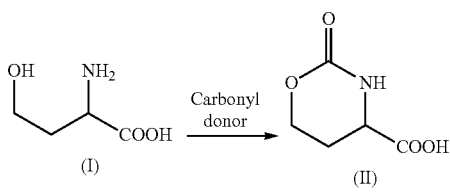

wherein:
the carbonyl donor chosen from urea, a urea derivative, a cyclic carbonate, a dialkyl carbonate, a diaryl carbonate, an alkyl carbamate, an aryl carbamate, and a halocarbonyl.

The process commences with formation of a reaction mixture comprising the compound comprising Formula (I), the carbonyl donor, an optional catalyst, and a solvent.

Numerous carbonyl donors are suitable for use in this process. In one embodiment, the carbonyl donor may be urea or a derivative of urea. Non-limiting examples of urea derivatives include dimethyl urea, tetramethyl urea, alkyl ureas, dialkyl ureas, tetralkyl ureas, aryl ureas, and the like. In another embodiment, the carbonyl donor may be a cyclic carbonate. Suitable cyclic carbonates include, but are not limited to, ethylene carbonate, propylene carbonate, a butylene carbonate, a pentylene carbonate, and so forth. In yet another embodiment, the carbonyl donor may be a dialkyl carbonate such as, e.g., dimethyl carbonate, diethyl carbonate, dipropyl carbonate, and so forth. In a further embodiment, the carbonyl donor may be a diaryl carbonate (such as, e.g., diphenyl carbonate) or an alkyl aryl carbonate. In an alternate embodiment, the carbonyl donor may be an alkyl carbamate (such as, e.g., methyl carbamate) or an aryl carbamate (such as, e.g., phenyl carbamate). In yet another embodiment, the carbonyl donor may be a halocarbonyl compound. Non-limiting examples of suitable halocarbonyl compounds include phosgene (also known as carbonyl dichloride), diphosgene, triphosgene, methyl chloroformate, ethyl chloroformate, propyl chloroformate, isobutyl chloroformate, and the like.

Suitable molar ratios of the compound comprising Formula (I) and the carbonyl donor are presented above in section (I)(a)(i). The optional base and concentrations thereof are discussed above in section (I)(a)(i). The optional catalyst and concentrations thereof are detailed above in section (I)(a)(ii). Similarly, suitable solvents and concentrations thereof are presented above in section (I)(a)(iii). The compound comprising Formula (I) is contacted with the carbonyl donor to form a carbamate, i.e., the compound comprising Formula (II) under conditions detailed above in section (I)(b).

(III) Preparation of a Compound Comprising Formula (III)

A further aspect of the disclosure provides a process in which a compound comprising Formula (II) is contacted with a compound comprising MeZ to form the compound comprising Formula (III) or a pharmaceutically acceptable salt thereof, according to the reaction scheme shown below:

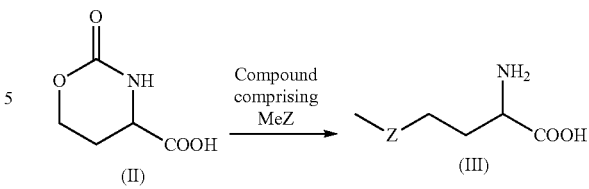

wherein:
Me is methyl; and
Z is sulfur or selenium.

The process commences with formation of a reaction mixture comprising the compound comprising Formula (II), a compound comprising MeZ, and a solvent.

A variety of compounds comprising MeZ are suitable for use in this process. In some embodiments, the compound comprising MeZ may be an alkali metal methanethiolate as detailed above in section (I)(c)(i). In other embodiments, the compound comprising MeZ may be methyl mercaptan as described above in section I)(c)(ii). In further embodiments, the compound comprising MeZ may be an alkali metal methaneselenoate as detailed above in section (I)(c)(iii). In still other embodiments, the compound comprising MeZ may be methyl selenol as described above in (I)(c)(iv).

The compound comprising Formula (II) is contacted with a compound comprising MeZ to form the compound comprising Formula (III) or a pharmaceutically acceptable salt thereof under conditions detailed above in section (I)(d). The final product may be isolated, and/or converted to a free acid or a salt, as detailed above in section (I)(d).

Definitions

To facilitate understanding of the invention, several terms are defined below.

The term "acyl," as used herein alone or as part of another group, denotes the moiety formed by removal of the hydroxy group from the group COOH of an organic carboxylic acid, e.g., RC(O), wherein R is $R^1$, $R^1O—$, $R^1R^2N—$, or $R^1S—$, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl," "substituted alkyl," "substituted alkenyl," "substituted aryl," and "substituted heteroaryl" moieties described herein are hydrocarbyl, alkyl, alkenyl, aryl, and heteroaryl moieties, respectively, that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, keto, acyl, acyloxy, nitro, amino, amido, nitro, cyano, thiol, ketals, acetals, esters, and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds and processes without departing from the scope of the invention, it is intended that all matter contained in the above description and in the examples given below, shall be interpreted as illustrative and not in a limiting sense.

EXAMPLES

The following examples detail various embodiments of the invention.

Example 1

Synthesis of Methionine via a Carbamate Intermediate

Approximately 1 equivalent of homoserine, 1 equivalent of phosgene, 2 equivalents of triethylamine and 10 equivalents of THF may be added to a reactor. The reactor may be heated to 30° C. for about 3 hours to generate the carbamate intermediate.

A solution of sodium methanethiolate may be prepared by adding 1.1 equivalents of methyl mercaptan to a slurry of 1.1 equivalents of sodium hydroxide in DMF. The solution may be stirred for 1 hour.

The solution of sodium methanethiolate may be added to the reactor containing the carbamate solution. The reactor may be heated to about 80° C. for about 2 hr. The solvent (DMF) may be removed by distillation. Water may be added to the resultant solution comprising the sodium salt of methionine. The aqueous solution then may be washed with methyl isobutyl ketone (MIBK) to remove impurities.

The solution of the sodium salt of methionine may be treated with water and 37% HCL (2.5 equivalents). The solution may be cooled and washed with MIBK. The pH of the solution may be adjusted to 5.7 with NaOH. The precipitated methionine may be isolated by filtration. The mother liquor may be concentrated, wherein the sodium chloride precipitates. After removal of the sodium chloride by filtration at 95° C., the filtrate may be cooled such that additional methionine precipitates. The second crop of methionine may be isolated and washed with cold water.

Example 2

Synthesis of Methionine via a Cyclic Carbamate

Homoserine ethyl carbamate: Homoserine (20 g, 168 mmol) and sodium bicarbonate (29.6 g, 353 mmol) were mixed together in water (150 mL). The mixture was heterogeneous. The ethyl chloroformate (17.6 mL, 185 mmol) was added over 20 minutes. The mixture was stirred an additional 30 minutes after the addition. Gas evolution had ceased and the mixture was homogeneous. The mixture was chilled with an ice bath. Ethyl acetate (50 mL) was added. Concentrated HCl (12.5 mL) was slowly added. Sodium chloride (30 g) was added. The phases were separated. The aqueous phase was extracted with ethyl acetate (3×50 mL). The four organic extracts were combined, dried and concentrated. A white solid (16 g; 90% assay) was obtained.

Cyclic carbamate: Homoserine ethyl carbamate (10 g, 52 mmol) was suspended in t-butanol (200 mL) and heated to 50° C. The mixture was homogeneous. Sodium t-butoxide (10.6 g, 110 mmol) was gradually added. The addition was mildly exothermic and the mixture was heterogeneous. Analysis indicated the reaction was done within two hours. The solvent was removed from the mixture using a rotary evaporator. The solid residue was taken up in isopropanol (150 mL) and the heated to reflux. The mixture was filtered hot and the solid was washed with isopropanol. The solvent was removed from the filtrate using a rotary evaporator. The solid was titrated with acetonitrile at room temperature. The mixture was filtered and the solid was washed with acetonitrile. A white solid (6.1 g) was obtained with an LC purity of 97.7%.

Methionine: Cyclic carbamate (100 mg, 0.69 mmol) and sodium methanethiolate (150 mg, 2.14 mmol) were mixed together in DMSO (2 mL) and heated to 150° C. After two hours the mixture was diluted to 25 mL with water. HPLC analysis indicated 16% molar yield of methionine.

Example 3

Synthesis of Methionine via a Cyclic Carbamate

Cyclic carbamate: Homoserine ethylcarbamate (2 g, 10.5 mmol) was dissolved in anhydrous DMF (20 mL) and heated to 65° C. 1 M potassium t-butoxide/THF (21 mL, 21 mmol) was added over 15 minutes. More DMF (10 mL) was added and the temperature was increased to 85° C. Analysis indicated the reaction was done within four hours. 1 M HCl (21 mL) was added to the reaction mixture. The solvent was removed using a rotary evaporator. The crude product was purified using normal phase chromatography (40 g-silica gel cartridge/0-40% $CH_3OH$-EtOAc). The product-containing fractions were combined and the solvent was removed using a rotary evaporator. The residue was taken up in ethyl acetate and the product precipitated. The mixture was filtered and the solid was washed with ethyl acetate. 930 mg (61% yield) of a white solid was obtained.

Methionine: The cyclic carbamate (100 mg, 0.69 mmol) and $NaSCH_3$ (101 mg, 1.45 mmol) were mixed together in 2 mL of DMF and heated to 80° C. for 2 hours. Chromatographic analysis indicated that methionine was the major product.

What is claimed is:

1. A process for preparing a compound comprising Formula (III) or a pharmaceutically acceptable salt thereof, the process comprising:

a. contacting a compound comprising Formula (I) with a carbonyl donor, wherein the carbonyl donor is chosen from a urea, a urea derivative, a cyclic carbonate, a dialkyl carbonate, a diaryl carbonate, an alkyl carbamate, an aryl carbamate, and a halocarbonyl to form a compound comprising Formula (II); and b. contacting the compound comprising Formula (II) with a compound comprising MeZ to form the compound comprising Formula (III) or the pharmaceutically acceptable salt thereof:

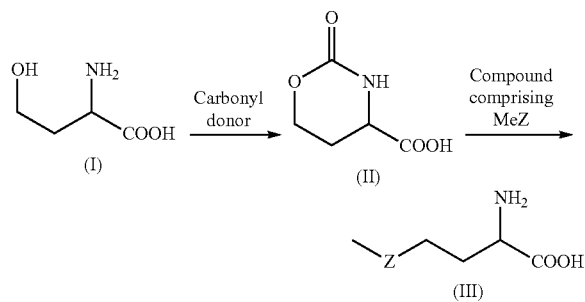

wherein:
Me is methyl; and
Z is sulfur or selenium.

2. The process of claim 1, wherein the molar ratio of the compound comprising Formula (I) to the carbonyl donor is from about 1:0.1 to about 1:10.

3. The process of claim 1, wherein step (a) is conducted in the presence of a base; and the molar ratio of the compound comprising Formula (I) to the base is from about 1:0.1 to about 1:10.

4. The process of claim 1, wherein step (a) is conducted in the presence of a catalyst; and the molar ratio of the compound comprising Formula (I) to the catalyst is from about 1:0.001 to about 1:1.

5. The process of claim 1, wherein step (a) is conducted in the presence of a solvent chosen from acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, water, a C1-C4 alcohol, propylene glycol, and combinations thereof.

6. The process of claim 5, wherein the molar ratio of the solvent to the compound comprising Formula (I) is from about 1:1 to about 50:1.

7. The process of claim 1, wherein step (a) is conducted at a temperature from about 20° C. to about 200° C. and at a pressure from about 0 psig to about 50 psig.

8. The process of claim 1, wherein the compound comprising MeZ is chosen from an alkali metal methanethiolate, an alkali metal methaneselenoate, methyl mercaptan, and methyl selenol.

9. The process of claim 8, wherein the alkali metal is chosen from sodium, potassium, and lithium.

10. The process of claim 8, wherein the molar ratio of the compound comprising Formula (II) to the alkali metal methanethiolate or the alkali metal methaneselenoate is from about 1:0.25 to about 1:5.

11. The process of claim 8, wherein the molar ratio of the compound comprising Formula (II) to methyl mercaptan or methyl selenol is from about 1:10 to about 1:150.

12. The process of claim 1, wherein step (b) is conducted in the presence of a solvent chosen from acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, water, a C1-C4 alcohol, propylene glycol, and combinations thereof.

13. The process of claim 12, wherein the molar ratio of the solvent to the compound comprising Formula (II) is from about 1:1 to about 50:1.

14. The process of claim 1, wherein step (b) is conducted at a temperature from about 20° C. to about 200° C., at ambient pressure, and under an inert gas chosen from nitrogen and argon.

15. The process of claim 1, wherein the compound comprising Formula (III) or the pharmaceutically acceptable salt thereof has an L configuration, a D configuration, or mixture thereof.

16. The process of claim 3, wherein the carbonyl donor is phosgene; the base is triethylamine; the molar ratio of the compound comprising Formula (I) to phosgene to triethylamine is about 1:1:1; step (a) is conducted in the presence of tetrahydrofuran as a solvent; the molar ratio of the solvent to the compound comprising Formula (I) is about 5:1; and step (a) is conducted at a temperature of about 30° C.

17. The process of claim 16, wherein the compound comprising MeZ is sodium methanethiolate; the molar ratio of the compound comprising Formula (II) to sodium methanethiolate is about 1:1.1; step (b) is conducted in the presence of N,N-dimethylformamide as a solvent; the molar ratio of the solvent to the compound comprising Formula (II) is about 10:1; and step (b) is conducted at a temperature of about 80° C.

18. The process of claim 1, wherein the carbonyl donor is ethylene carbonate; the molar ratio of the compound comprising Formula (I) to ethylene carbonate is about 1:1; step (a) is conducted the presence of magnesium oxide as a catalyst and ethanol as a solvent; the molar ratio of the compound comprising Formula (I) to the catalyst is about 1:0.15; the molar ratio of the solvent to the compound comprising Formula (I) is about 10:1; and step (a) is conducted at a temperature of about 80° C.

19. A process for preparing a compound comprising Formula (III) or a pharmaceutically acceptable salt thereof, the process comprising contacting a compound comprising Formula (II) with a compound comprising MeZ to form the compound comprising Formula (III) or the pharmaceutically acceptable salt thereof:

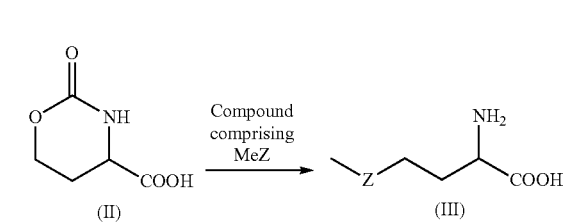

wherein:
Me is methyl; and
Z is sulfur or selenium.

20. The process of claim 19, wherein the compound comprising MeZ is chosen from an alkali metal methanethiolate, an alkali metal methaneselenoate, methyl mercaptan, and methyl selenol.

21. The process of claim 20, wherein the alkali metal is chosen from sodium, potassium, and lithium.

22. The process of claim 20, wherein the molar ratio of the compound comprising Formula (II) to the alkali metal methanethiolate or the alkali metal methaneselenoate is from about 1:0.25 to about 1:5.

23. The process of claim 20, wherein the molar ratio of the compound comprising Formula (II) to methyl mercaptan or methyl selenol is from about 1:10 to about 1:150.

24. The process of claim 19, wherein the reaction is performed in the presence of a solvent chosen from acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, water, a C1-C4 alcohol, propylene glycol, and combinations thereof.

25. The process of claim 24, wherein the molar ratio of the solvent to the compound comprising Formula (II) is from about 1:1 to about 50:1.

26. The process of claim 19, wherein the process is conducted at a temperature from about 20° C. to about 200° C., at ambient pressure, and under an inert gas chosen from nitrogen and argon.

27. The process of claim 19, wherein the compound comprising Formula (III) or the pharmaceutically acceptable salt thereof has an L configuration, a D configuration, or mixture thereof.

28. The process of claim 19, wherein the compound comprising MeZ is sodium methanethiolate; the molar ratio of the compound comprising Formula (II) to sodium methanethiolate is about 1:1.1; the reaction is conducted in the presence of N,N-dimethylformamide as a solvent; the molar ratio of the solvent to the compound comprising Formula (II) is about 10:1; and the reaction is conducted at a temperature of about 80° C.

* * * * *